United States Patent [19]
Leight

[11] Patent Number: 6,148,446
[45] Date of Patent: Nov. 21, 2000

[54] MULTI-POSITION BANDED EARMUFF

[75] Inventor: Howard S. Leight, San Diego, Calif.

[73] Assignee: Bacou USA Safety, Inc., San Diego, Calif.

[21] Appl. No.: 09/550,759

[22] Filed: Apr. 17, 2000

Related U.S. Application Data

[63] Continuation-in-part of application No. 09/306,324, May 6, 1999, abandoned.

[51] Int. Cl.[7] .................................................. A61F 11/14
[52] U.S. Cl. ............................. 2/209; 181/129; 128/867
[58] Field of Search ....................... 2/209, 423; 128/864, 128/866, 867; 181/129, 128; D29/112; D14/205; 381/71.6, 72, 371, 372, 376, 378, 379

[56] References Cited

U.S. PATENT DOCUMENTS

| | | | |
|---|---|---|---|
| D. 237,307 | 10/1975 | Miyamoto et al. ................... | D14/205 |
| D. 266,417 | 10/1982 | Perez ................................... | D14/205 |
| D. 317,767 | 6/1991 | Banks .................................. | D14/205 |
| D. 324,386 | 3/1992 | Oblinger ............................. | D14/205 |
| 1,527,802 | 2/1925 | Miyamoto et al. ................... | D14/205 |
| 2,345,842 | 4/1944 | Valentine ............................. | 128/866 |
| 2,437,049 | 3/1948 | Salisbury et al. .................... | 128/866 |
| 2,603,724 | 7/1952 | Kettler ................................. | 181/129 |
| 3,562,816 | 2/1971 | Hutchinson ......................... | 2/209 |
| 3,845,505 | 11/1974 | Davison et al. ..................... | 2/209 |
| 4,437,538 | 3/1984 | Ohlsson et al. ..................... | 181/129 |
| 4,471,496 | 9/1984 | Gardner, Jr. et al. ................ | 2/209 |
| 5,018,599 | 5/1991 | Dohi et al. .......................... | 181/129 |
| 5,023,955 | 6/1991 | Murphy, II et al. ................. | 2/209 |
| 5,068,923 | 12/1991 | Sjoqvist .............................. | 2/209 |
| 5,243,709 | 9/1993 | Sheehan et al. ..................... | 2/209 |
| 5,406,037 | 4/1995 | Nageno et al. ...................... | 181/129 |
| 5,500,958 | 3/1996 | Falco ................................... | 2/209 |
| 5,519,783 | 5/1996 | Kumar ................................. | 181/129 |
| 5,996,123 | 12/1999 | Leight et al. ........................ | 2/209 |

FOREIGN PATENT DOCUMENTS

| | | | |
|---|---|---|---|
| 2706382 | 2/1976 | Germany ............................. | 2/209 |

*Primary Examiner*—Amy B. Vanatta
*Attorney, Agent, or Firm*—Leon D. Rosen

[57] ABSTRACT

A noise-blocking banded earmuff wherein the earmuffs (12, 14) are fixed against rotation about a horizontal axis (34) with respect to the band (24), and wherein the band can extend upwardly around the top of the head, downwardly (24A) around the neck, or rearwardly (24B) behind the head, using earmuffs of moderate size. Instead of each earmuff aperture being of a vertically elongated oval shape, each aperture has four 90° concave corner segments (46–49) lying at the corners of an imaginary square (36), and four connecting segments (41–44) that each connects two concave segments. The middles (56) of the connecting segments lie closer to the aperture axis (34) than the middles (50) of the concave corner sections. The connecting segments can be largely straight to form an earmuff aperture of largely square shape with rounded corners. The connecting segments can be convex (181–184) to form an earmuff aperture of largely cloverleaf shape. The shell (70) of the earmuff can have a pair of horizontally-spaced grooves (76) that each extends vertically in an initial orientation, with mounts lying in the grooves and pivotally connected to the shell.

14 Claims, 3 Drawing Sheets

U.S. Patent      Nov. 21, 2000      Sheet 1 of 3      6,148,446
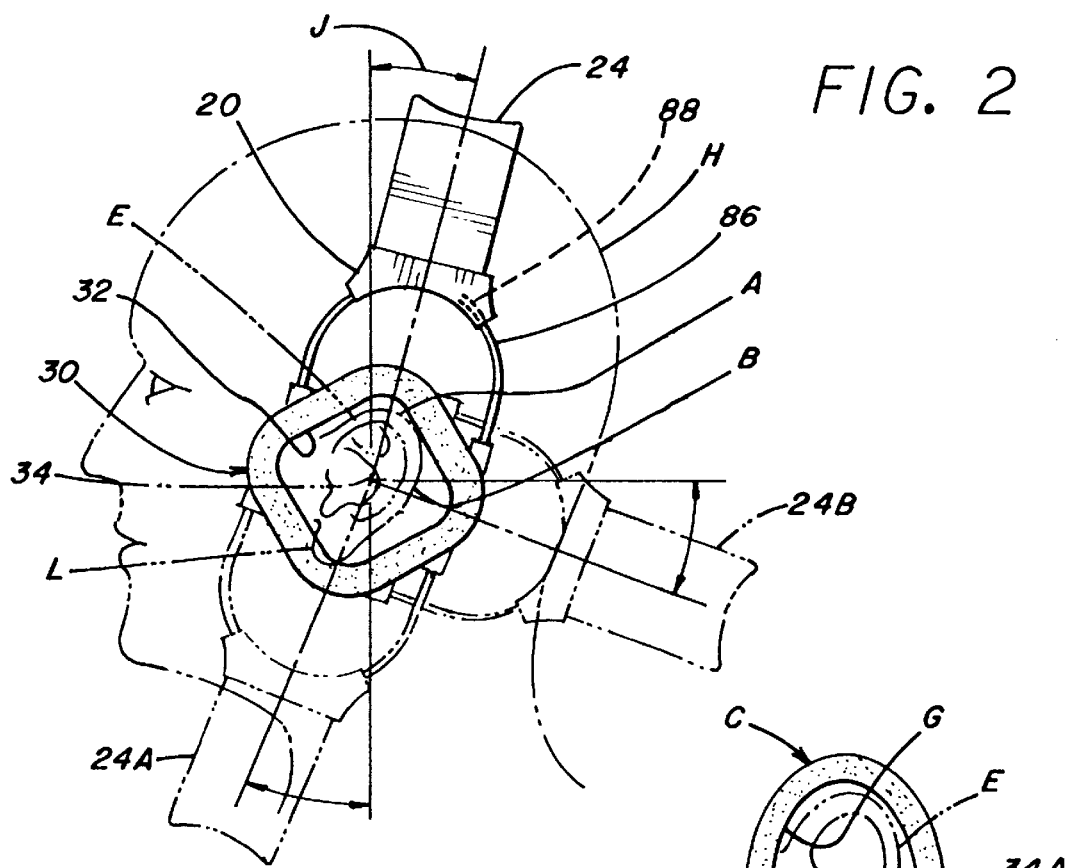
FIG. 2
FIG. 1 PRIOR ART
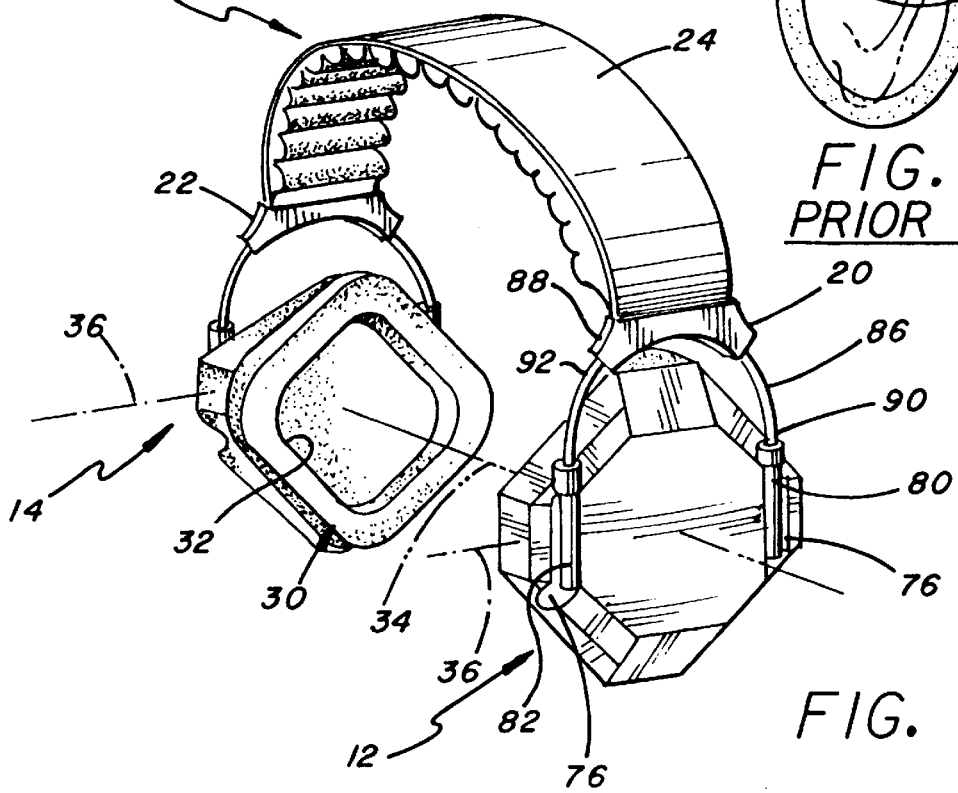
FIG. 3

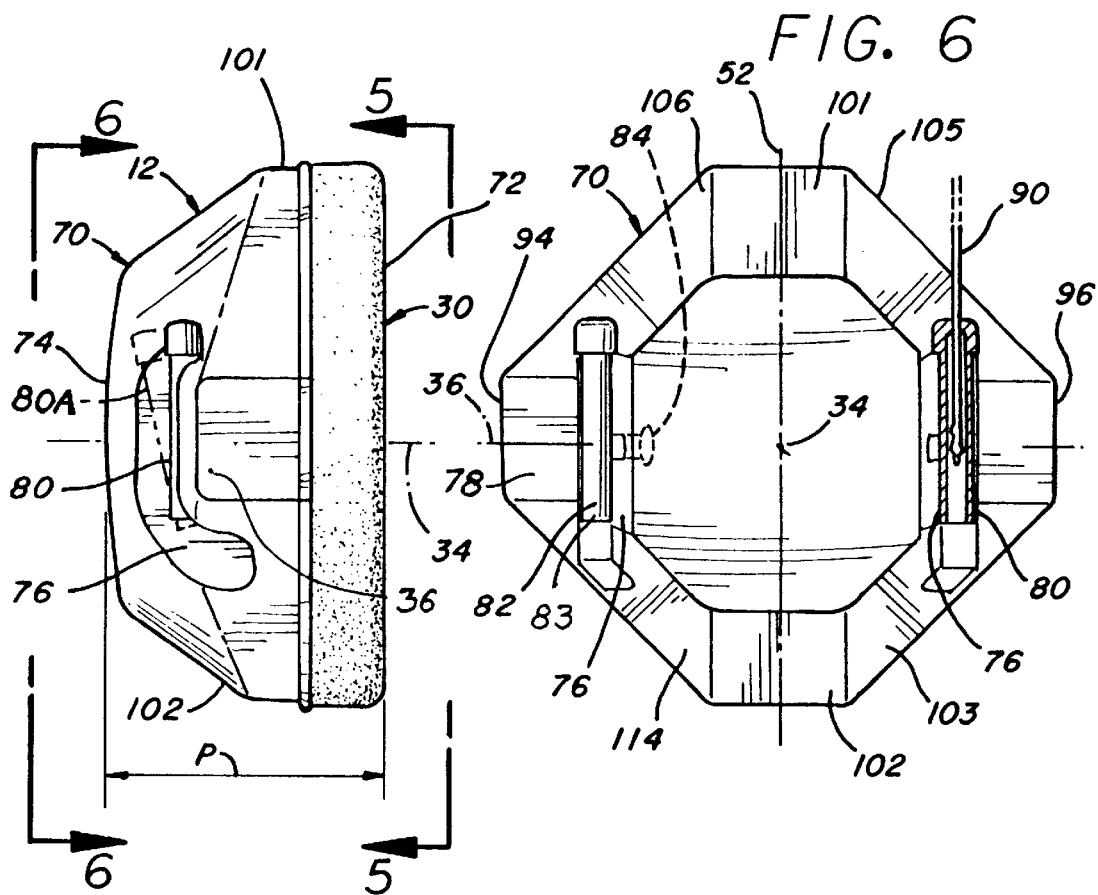
FIG. 6
FIG. 4
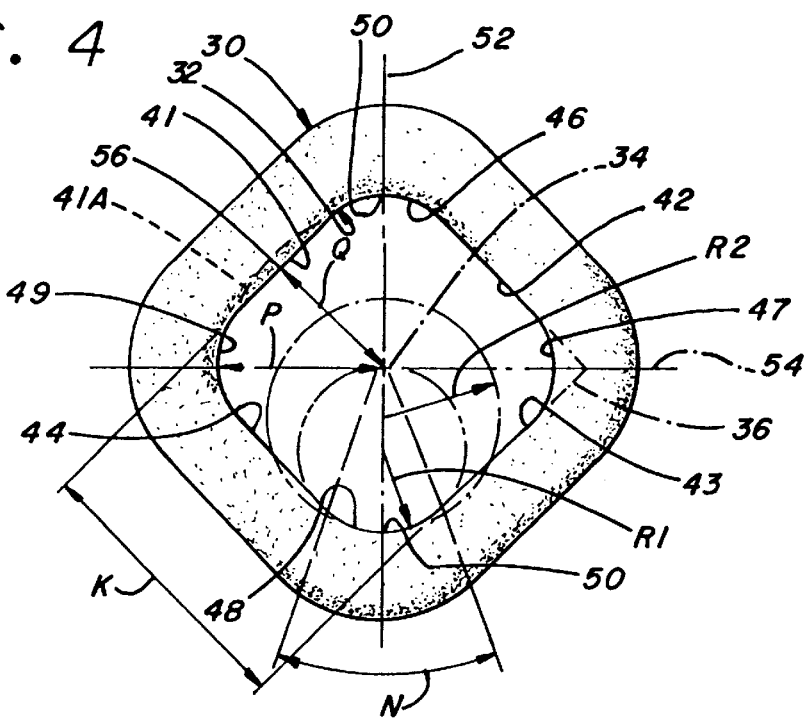
FIG. 5

MULTI-POSITION BANDED EARMUFF

CROSS-REFERENCE

This is a continuation-in-part of U.S. patent application Ser. No. 09/306,324 filed May 6, 1999 now abandoned.

BACKGROUND OF THE INVENTION

Noise-blocking banded earmuff devices include earmuffs with apertures that each receives the upper and middle part of the outer ear of a person, with the earlobe being pressed inwardly by the cushion that surrounds the aperture. Most cushion apertures are in the form of elongated ovals that efficiently receive the middle and upper parts of the outer ear. Usually, the band extends around the top of the person's head, or is angled backward by several degrees from an upward direction. Sometimes a person wishes to wear the band under his chin, which the elongated oval aperture allows. However, sometimes a person wishes to wear the band so it extends behind his head. If the earmuff cannot rotate on the band, then wearing the band behind a person's head results in the top of the outer ear being pressed inwardly by the cushion, which is generally uncomfortable and which reduces sound blocking. While the earmuffs can be mounted so they can rotate on the band ends, this adds to cost and size, especially if rugged mounting is to be achieved. A banded earmuff device that allows the band to extend behind a person's head as well as above the head and below the chin, without the earmuffs being rotatably mounted on the band ends, and using earmuffs of moderate size, would be of value.

SUMMARY OF THE INVENTION

In accordance with one embodiment of the present invention, a band earmuff device is provided with earmuff apertures that can be turned about 90° and 180° from an initial position, and still receive the upper and middle portions of a person's outer ear, in an earmuff of simple and low cost construction. This allows the band, whose opposite ends are prevented from rotating about a horizontal earmuff aperture axis relative to the earmuffs, to be worn so the band extends primarily above the head of the person, below the chin of the person, or behind the head of the person, with the ear comfortably received in the aperture at any of these positions. Each earmuff aperture has a height and a perpendicular width that are about the same, so each earmuff can receive about the same amount of the ear when turned about 90° or 180° from an initial position.

Each aperture includes concave corner segments lying at the four corners of an imaginary square, with connecting segments connecting the concave segments. The distance from the axis of the aperture to the middle of each concave corner segments is greater than the distance from the axis to the middle of each connecting segment. In one earmuff, the connecting segments are substantially straight to leave an earmuff aperture of largely square shape, with four concave corners. In another aperture, the connecting segments are convex, to form an earmuff aperture of cloverleaf shape.

The shell of each earmuff can be provided with vertical grooves at its front and rear, with vertically-elongated mounts received in each groove. This results in the mounts being protected, especially when the mounts can pivot with respect to the shell, and results in an enhanced appearance because the simple mounts are largely surrounded by the walls of the grooves.

The novel features of the invention are set forth with particularity in the appended claims. The invention will be best understood from the following description when read in conjunction with the accompanying drawings.

BRIEF DESCRIPTION OF THE DRAWINGS

FIG. 1 is a side elevation view of an earmuff of the prior art, and showing, in phantom lines, how a person's outer ear fits into the earmuff aperture.

FIG. 2 is a sectional side view of a band earmuff apparatus constructed in accordance with the present invention, and showing, in phantom lines, a person who is wearing the earmuff and showing how the earmuff can be worn in three different positions angled about 90° apart.

FIG. 3 is a perspective view of the band earmuff apparatus of FIG. 2, with the band expanded to fit on a person's head.

FIG. 4 is a side elevation view of one of the earmuffs of the band earmuff apparatus of FIG. 3, without the band mounted thereon.

FIG. 5 is an inner elevation view of the earmuff of FIG. 4, taken on line 5—5 thereof.

FIG. 6 is an outer elevation view of the earmuff of FIG. 4, taken on line 6—6 thereof.

DESCRIPTION OF THE PREFERRED EMBODIMENTS

Figure 7:
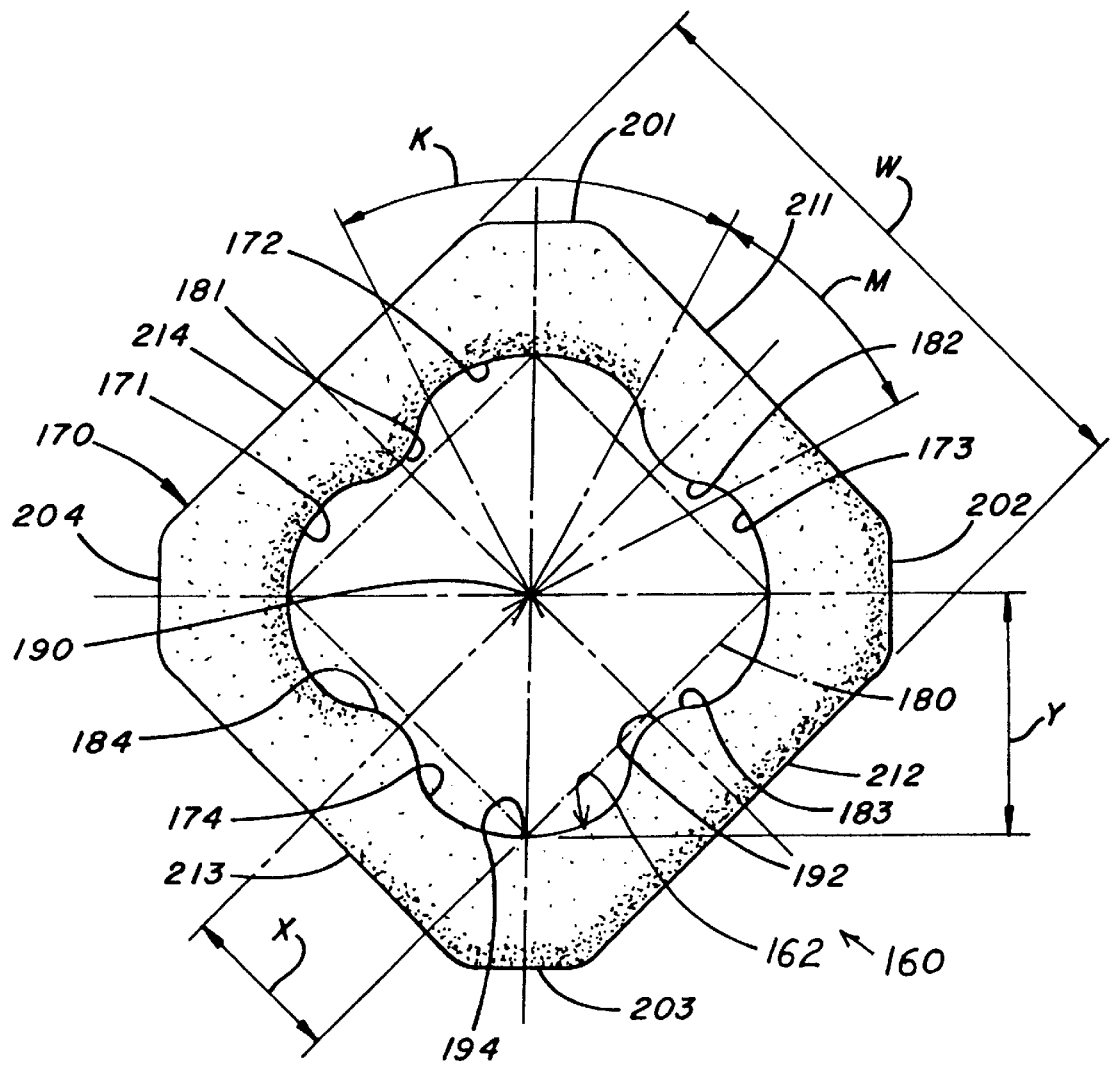
FIG. 7 is an inner elevation view of a cushion of an earmuff constructed in accordance with another embodiment of the invention, where the cushion aperture is of cloverleaf shape.

FIG. 3 illustrates a band earmuff apparatus 10 of the present invention, which includes a pair of earmuffs 12, 14 that are mounted on the ends 20, 22 of a band 24 or other holding device that fits on the head. Each earmuff has a cushion 30 with an aperture 32 for receiving most of the outer ear of a person. FIG. 2 shows the apparatus mounted on the head H of a person, with most of the outer ear of the person received within the aperture 32 of the earmuff cushion 30. The upper and middle portions A, B of the outer ear are moderately stiff, and it is uncomfortable to press them tightly against the sides of the person's head, so they are commonly received within the earmuff aperture. However, the lower end of the outer ear forms an earlobe L which can be pressed against the person's head without discomfort or loss of noise blocking capacity. It is common to press the cushion against the earlobe, to reduce the size of the earmuff.

Perhaps the most common position of the band 24 is as shown in solid lines in FIG. 2, with the band lying on top of the person's head, but tilted back by several degrees, with an angle J of 14° being shown. It is common for a person to wear the earmuff apparatus with the band having the orientation shown at 24A, where the band extends under the person's neck. It is also sometimes desirable for a person to wear the band apparatus with the band extending behind the person's head, as shown at 24B.

FIG. 1 shows an earmuff cushion C of the prior art, and shows how an ear E fits into the aperture G of the cushion. The vertically elongated oval shape of the prior art aperture G is efficient in receiving the ear and allowing an earmuff of small size to be used. However it does not allow the human outer ear to be comfortably received in the aperture if the aperture is turned 90°, wherein the band has the orientation shown at 24B in FIG. 2. It is noted that some earmuffs are mounted so they can pivot about a horizontal axis 34 or 34A on an end of the band; however, this adds to the size and cost of the band earmuff apparatus, especially if the pivotable connection is to be rugged. It is also noted (FIG. 3) that each of the earmuffs is pivotally connected about a second horizontal axis 36 with respect to a band end such as 20, with each second axis 36 being perpendicular to the first axis 34 when the earmuffs are worn. Such pivoting about the axes 36 is necessary to allow the cushions 30 to press uniformly against the person's head.

As shown in FIG. 5, in one preferred construction the ear-receiving aperture 32 of each earmuff cushion 30 is of largely square shape, as viewed inward along the aperture axis 34. The aperture has four concave corner segments 46–49 lying at the four corners of an imaginary square 36. The aperture (the walls of the aperture) also has four connecting sections 41–44 which are substantially straight and which are equally spaced from the axis. This results in an earmuff aperture of largely square shape but with concave rounded corners. The distance P between the middle 50 of each concave corner segment and the aperture axis 34 is greater than the distance Q between the middle 56 of each connecting segment and the axis.

It is desirable that the concave corner segments 46–49 have a large radius of curvature R1. It is desirable that the radius of curvature R1 be about the same as the radius of curvature at the top of the human outer ear, which is commonly about 20–25 mm, and which would lead to a radius R2 which is slightly greater than the radius R1 chosen by applicant for aesthetic purposes. The radius R1 is one-half the distance between a concave segment middle 50 and the axis 34 and is about 17 mm. The radius R1 is ¼th, or 25%, of the distance 2P between opposite concave segment middles 50. It is desirable that each concave segment extend by an angle N of at least 30° about the axis 34, to receive the top of the ear. It is preferred that the concave segments have a radius of curvature of at least ⅛th and preferably at least ¼th the distance between opposite extreme corners 50, or 25% or 50% of the distance from the axis 34 to the middle of the corner, so the earmuffs are not unduly enlarged for no good reason. Also, the large radius of curvature at the concave segments makes it more apparent to the wearer that his ear can fit into the segment. In the earmuff of FIG. 5 that applicant has designed, a distance K between opposite sides such as 41, 43 of the aperture is 58 mm with the distance 2P between opposite concave middles 50 being 68 mm. The connecting segments 41–44 are preferably largely straight, although they can have a slight curvature as indicated at 41A, with the radius of curvature of each connecting segment being greater than twice the radius of curvature R1 at a concave segment.

It is possible, to construct the cushion with an aperture that is round. However, such a construction has the disadvantage that it appears "bulky" and without sophisticated design, as compared to the design of FIG. 5. Also, a round design requires slightly more material.

FIG. 7 shows another earmuff 160 with an earmuff cushion 170 having an aperture 162 that includes four largely circular concave ear-receiving corner segments 171–174 that lie at the corners of an imaginary square 180. Each of the concave corner segments subtends an angle K of about 50°. Adjacent concave sections are joined by convex connection sections 181–184 that are convex (i.e. bulge toward the axis 190) and that each extends by an angle M of about 40°. The result is a cloverleaf design. The middles 192 of the connecting sections are spaced by a distance X from the axis that is less than the radial distance Y to the middle 194 of each corner section. Applicant has constructed earmuffs of the type illustrated in FIG. 7, with each cushion having an outside of largely octagonal shape (8 sides), but with shortened alternate sides 201–204 immediately outside the concave corner segments and longer sides 211–214 outside the connecting sections. The cushion has a width W of 3.39 inches (8.61 cm). Each concave corner section 171–174 has a radius of curvature of 0.787 inch (2.00 cm) while each connecting section 181–184 has a radius of curvature of 0.412 inch (1.05 cm), and the distance between opposite concave middles is about 7 cm. The cushion has a thickness of 0.65 inch (1.65 cm).

Since the earmuff cushion is used in only three orientations (with the band at 24, 24A and 24B in FIG. 2) it would be possible to provide concave corner sections at only three corners of the imaginary square. However, this would result in a different feeling at the earlobe at one of the three orientations, and is not preferred.

As shown in FIGS. 4 and 6, each earmuff such as 12 includes a rigid plastic molded shell 70 with an inner end 72 on which the cushion 30 is mounted, and an outer end 74. As shown in FIG. 6, the shell has a pair of horizontally spaced grooves 76 in opposite surface side parts 78, with each groove extending primarily vertically, parallel to the vertical line 52, when the earmuff apparatus is in its initial orientation with the band extending around the top of a person's head, as shown at 24 in FIG. 2. A pair of vertically-elongated mounts 80, 82 each has a lower end 83 that lies in one of the grooves and is a pivotally connected about a horizontal axis 36 on the shell 70. When a mount pivots, as to the position 80A in FIG. 4, its upper end may move out of its groove.

As shown in FIGS. 2 and 3, the particular band shown includes a U-shaped wire 86 that has its middle 88 fixed to a band end such as 20, and has opposite legs 90, 92 that are straight and that are received in holes of the mounts 80, 82. As shown in FIG. 6, the mounts are in the form of sleeves, and the wire legs 90, 92 can slide up and down within the sleeves, with moderate friction. As a result, the band can be comfortably worn by people with different size heads. As discussed earlier, the mounts 80, 82 can pivot about the axes 36 on a corresponding one of the earmuff shells. Each mount such as 82 is provided with a flange 84 that lies within the shell, although other mounting approaches can be used.

In an approach that applicant has used in another banded earmuff, the vertically elongated mounts are rigid bars with lower ends that lie in the vertical grooves. Such rigid bars have lower ends pivotally connected at axes 36, and have upper ends pivotally connected about axes extending parallel to axes 36 but lying above the shells, to ends of a band. In that case, the band is adjustable in length. In such banded earmuff as well as the one illustrated, the lower ends of the mounts lie in vertical grooves of the shell, and the mounts pass through the tops of the groove when the earmuffs are pulled apart. Also, lower ends of the mounts are pivotally connected to the shell at axes that pass through the grooves.

It would be possible to pivotally mount the mounts 80, 82 so they lie beyond the opposite horizontally-spaced sides 94, 96 of the earmuff. However, this would expose the mounts to damage and result in a product that appeared to be of lower quality because the mounts were almost completely exposed. Applicant prefers to form the shell with a largely flat outer end 74 (radius of curvature of at least the inward-to-outward thickness P of the earmuff). Also, the top and bottom of the shell has facets 101–106 (FIG. 6) that are tapered about 30° from the axis 34. This reduces the volume of the earmuff.

While certain parts such as the grooves 76 are described as extending "vertically", and other parts such as axes 36 are described as extending "horizontally", to help describe the invention as it is illustrated, it should be understood that the earmuff apparatus can be used in many different orientations with respect to the Earth.

Thus, the invention provides a band earmuff apparatus, where the earmuffs are mounted on the band so the earmuffs cannot rotate about the axis 34 of their ear-receiving apertures with respect to the band, but which enables the band to be worn in the three most common positions using earmuffs of simple construction. Each earmuff has an aperture for receiving the top and middle of the outer ear, with each aperture having a height (along line 52 in FIG. 5) and a perpendicular width (along line 54) that are about the same, so the aperture can receive about the same portion of the outer ear when the earmuff is turned 90° or clockwise or counterclockwise from an initial position. The aperture has largely circular concave segments at the four corners of an imaginary square, and has four connecting segments that connect the concave segments. The distance between the axis of the aperture and the middle of each concave corner segment, is greater than the distance between the axis and the middle of each connecting segment. Where the connecting segments are substantially straight, this results in an earmuff aperture of largely square shape, with rounded corners. Where the connecting segments are convex, this results in an earmuff aperture of cloverleaf shape. The concave corner each have a radius of curvature that is at least 25% of the distance from the axis to the middle of the corner. The shell of the earmuff, to which the cushion is attached, has a pair of vertical grooves that each receives a mount that holds an end of the band, with the mounts being pivotally mounted on the shell about axes that pass through the grooves.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A band earmuff apparatus comprising:
   a pair of earmuffs that each has a cushion with an aperture for receiving the top and middle of the outer ear of a person;
   a connecting device that fits partially around the head of the person and that holds said earmuffs at the opposite ears of the person;
   each of said apertures has an axis and has four concave corner segments that lie at the corner of an imaginary square that is centered on said axis, with each concave corner segment having a middle and constructed to receive about the same amount of the ear when turned about 90° clockwise or counterclockwise from an initial position as when in said initial position, and with said aperture having four connecting segments that each joins two of said concave corner segments, with each connecting segment having a middle lying closer to said axis than said middles of said concave corner segments.

2. The apparatus described in claim 1 wherein:
   the aperture in each of said earmuffs is largely square, with said connecting segments forming four substantially straight perpendicular sides of about equal length and with said concave corner segments forming four rounded corners.

3. The apparatus described in claim 1 wherein:
   each of said concave corner segments has a radius of curvature that is at least 25% of the distance from said axis to the middle of the concave corner segment.

4. The apparatus described in claim 1 wherein:
   each of said connecting sections is convex, to form an aperture of largely cloverleaf shape.

5. The apparatus described in claim 1 wherein:
   each of said earmuffs includes a rigid shell having inner and outer surfaces, with said cushions each fixed to the inner surface of one of said shells;
   the outer surface of each shell has a pair of primarily vertical grooves, and said connecting device has opposite ends that each includes a pair of mounts with lower ends lying in a pair of grooves of a shell and pivotally connected to the shell.

6. The apparatus described in claim 1 wherein:
   each of said earmuffs includes a rigid shell having inner and outer surfaces, with each cushion fixed to one of said inner surfaces;
   each shell outer surface has a periphery with eight sides arranged in a largely octagonal shape, but with short sides lying outside said cushion concave corner segments and with longer sides that are longer than said short sides and that lie outside said cushion connecting segments.

7. A band earmuff apparatus which includes a pair of earmuffs that each has a cushion with an aperture for receiving most of the outer ear of a person, and a connecting device that fits partially around the head of the person to hold said earmuffs at the person's ears, wherein:
   each of said earmuff apertures has an axis, with each earmuff aperture having four concave corner segments spaced 90° apart about said axis and having concave corner segment middles radially spaced from said axis, and with each earmuff aperture having four connecting segments that each connects two of said concave corner segments and that each has a connecting segment middle radially spaced from said axis, with said concave corner segment middles spaced further from said axis than said connecting segment middles.

8. The apparatus described in claim 7 wherein:
   each of said earmuff apertures is of largely square shape, with said connecting segments forming sides of the square and said concave corner segments forming rounded corners of the square, with each of said sides of the square having a radius of curvature that is at least twice the radius of curvature of one of said concave corner segments.

9. The apparatus described in claim 7 wherein:
   the radius of curvature at each of said concave corner segments is about one-half the distance between said axis and the middle of the concave corner segment.

10. The apparatus described in claim 7 wherein:
    each of said connecting segments is convex, to form a largely cloverleaf aperture.

11. The apparatus described in claim 7 wherein:
    each of said earmuffs includes a shell with inner and outer surfaces, with each of said cushions mounted on the inner surface of one of said shells;
    each of said shell outer surfaces has a pair of horizontally-spaced grooves that each extends vertically in an initial orientation of said apertures wherein said connecting device extends around the top of the head of the person, and including a pair of vertically elongated mounts lying at least partially in each pair of grooves of a shell and pivotally connected to the shell.

12. The apparatus described in claim 11 wherein:
    the outer surface of each of said shells has a center surface portion that faces primarily outwardly, as seen when viewed along said axis of said aperture toward said center surface portion, and with said outer surface having a radially outer area which lies radially outside said center surface portion and within said periphery, and that has top and bottom surface parts that are angled about 45° from said axis, and with opposite side parts and with said grooves being formed in said opposite side parts.

13. A band earmuff apparatus comprising a pair of earmuffs that each has a cushion and a holding device that fits partially around the head of a person to hold said earmuffs at the person's ears, wherein:

each of said earmuffs includes a shell with inner and outer ends, with one of said cushions mounted on the shell inner end;

each of said shell outer ends has a pair of horizontally-spaced grooves that each extends substantially vertically in an initial orientation of said apertures wherein said holding device extends around the top of the head of the person, and including a pair of vertically elongated mounts with lower portions lying in said grooves and pivotally connected to said shell.

14. The apparatus described in claim 13 wherein:

each of said shells has an even and primarily outwardly-facing center surface and has a periphery, as viewed along an axis of an aperture in said cushion toward said shell, and with a radially outer area of said shell which lies radially outside said center surface and within said periphery, having top and bottom parts that are angled from said axis, and with opposite sides and with said grooves being formed in said opposite sides.

* * * * *